(12) United States Patent
Ostrovsky et al.

(10) Patent No.: US 9,011,489 B2
(45) Date of Patent: Apr. 21, 2015

(54) SURGICAL COMPOSITE BARBED SUTURE

(75) Inventors: Isacc Ostrovsky, Wellesley, MA (US); Hamid Davoudi, Westwood, MA (US); Jianmin (Jamie) Li, Lexington, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1041 days.

(21) Appl. No.: 12/394,965

(22) Filed: Feb. 27, 2009

(65) Prior Publication Data
US 2009/0287245 A1 Nov. 19, 2009

Related U.S. Application Data

(60) Provisional application No. 61/071,726, filed on May 14, 2008.

(51) Int. Cl.
*A61B 17/04* (2006.01)
*A61B 17/06* (2006.01)

(52) U.S. Cl.
CPC ... *A61B 17/06166* (2013.01); *A61B 2017/0412* (2013.01); *A61B 2017/0458* (2013.01); *A61B 2017/06176* (2013.01)

(58) Field of Classification Search
USPC .................. 606/228, 151, 232; 43/1, 42, 100
See application file for complete search history.

(56) References Cited

U.S. PATENT DOCUMENTS

| 527,263 | A | 10/1894 | Blanchard |
| 4,221,212 | A | 9/1980 | Miller |
| 4,583,540 | A | 4/1986 | Malmin |
| 4,735,615 | A | 4/1988 | Uddo et al. |
| 5,085,661 | A | 2/1992 | Moss |
| 5,149,329 | A | 9/1992 | Richardson |
| 5,217,438 | A | 6/1993 | Davis et al. |
| 5,292,327 | A | 3/1994 | Dodd et al. |
| 5,312,422 | A | 5/1994 | Trott |
| 5,499,991 | A | 3/1996 | Garman et al. |
| 5,571,119 | A | 11/1996 | Atala |
| 5,891,168 | A * | 4/1999 | Thal ............................ 606/232 |

(Continued)

FOREIGN PATENT DOCUMENTS

| DE | 202007015955 U1 | 3/2009 |
| FR | 2 422 386 A | 11/1979 |

(Continued)

OTHER PUBLICATIONS

International Preliminary Report on Patentability for PCT Patent Application No. PCT/US2009/040587, mailed on Nov. 25, 2010, 10 pages.

(Continued)

*Primary Examiner* — Gregory Anderson
*Assistant Examiner* — Christina Lauer

(57) ABSTRACT

In one embodiment, a medical device includes an elongate member configured to be inserted into a body. The elongate member has a first end portion and a second end portion opposite the first end portion. The elongate member includes a retaining member extending from the elongate member. The retaining member is configured to anchor the elongate member with respect to bodily tissue. The first end portion of the elongate member includes a coupling portion configured to be coupled to a filament. The second end portion of the elongate member includes a coupling portion configured to be coupled to the filament.

20 Claims, 5 Drawing Sheets

(56) References Cited

U.S. PATENT DOCUMENTS

| | | | |
|---|---|---|---|
| 5,931,855 A | | 8/1999 | Buncke |
| 5,984,933 A | * | 11/1999 | Yoon ............................ 606/232 |
| 6,200,330 B1 | * | 3/2001 | Benderev et al. ............ 606/232 |
| 6,306,156 B1 | | 10/2001 | Clark |
| 6,398,787 B1 | * | 6/2002 | Itoman ......................... 606/103 |
| 6,635,058 B2 | | 10/2003 | Beyar et al. |
| 6,848,152 B2 | | 2/2005 | Genova et al. |
| 7,377,926 B2 | | 5/2008 | Topper et al. |
| 7,381,212 B2 | | 6/2008 | Topper et al. |
| 2001/0037119 A1 | | 11/2001 | Schmieding |
| 2001/0049467 A1 | | 12/2001 | Lehe et al. |
| 2003/0065336 A1 | | 4/2003 | Xiao |
| 2003/0171778 A1 | * | 9/2003 | Lizardi ......................... 606/232 |
| 2004/0087978 A1 | | 5/2004 | Velez et al. |
| 2004/0098053 A1 | * | 5/2004 | Tran ............................. 606/232 |
| 2004/0106847 A1 | | 6/2004 | Benderev |
| 2004/0237736 A1 | | 12/2004 | Genova et al. |
| 2005/0203576 A1 | | 9/2005 | Sulamanidze et al. |
| 2006/0282161 A1 | * | 12/2006 | Huynh et al. ................ 623/2.11 |
| 2007/0016135 A1 | | 1/2007 | Kanner et al. |
| 2007/0038249 A1 | | 2/2007 | Kolster |
| 2007/0129758 A1 | * | 6/2007 | Saadat ......................... 606/232 |
| 2008/0132931 A1 | | 6/2008 | Mueller |
| 2009/0076529 A1 | | 3/2009 | Ganti |
| 2010/0268255 A1 | | 10/2010 | Ostrovsky et al. |

FOREIGN PATENT DOCUMENTS

| | | | |
|---|---|---|---|
| JP | 2005532848 T | | 11/2005 |
| JP | 2006515204 T | | 5/2006 |
| JP | 2007532174 A | | 11/2007 |
| JP | 2007535335 A | | 12/2007 |
| WO | 0178609 A2 | | 10/2001 |
| WO | WO 2004/112585 A | | 12/2004 |
| WO | WO2004112585 | * | 12/2004 |
| WO | WO 2007/098212 A | | 8/2007 |
| WO | 2008020937 A2 | | 2/2008 |
| WO | 2008087635 A2 | | 7/2008 |
| WO | 2010121052 A2 | | 10/2010 |

OTHER PUBLICATIONS

International Search Report and Written Opinion for International Application No. PCT/US2009/040587, mailed on Oct. 21, 2009, 18 pages.
Restriction Requirement for U.S. Appl. No. 12/760,049, mailed Mar. 29, 2012, 9 pages.
Non-Final Office Action for U.S. Appl. No. 12/760,049, mailed Jun. 1, 2012, 17 pages.
Restriction Requirement Response for U.S. Appl. No. 12/760,049, filed Apr. 27, 2012, 2 pages.
International Search Report and Written Opinion for PCT Application No. PCT/US2010/031273, mailed on Dec. 1, 2010, 17 pages.
"Suture", Free Online Dictionary, Thesaurus and Encyclopedia, retrieved on May 21, 2012 from http://www.thefreedictionary.com/suture, 3 pages.
Non-Final Office Action Response for U.S. Appl. No. 12/760,049, filed Aug. 29, 2012, 8 pages.
Non-Final Office Action for U.S. Appl. No. 12/760,049, mailed Nov. 8, 2012, 21 pages.
RCE and Final Office Action Response for U.S. Appl. No. 12/760,049, filed Feb. 8, 2013, 11 pages.
Office Action for Japanese Application No. 2011-509522 (with English Translation), mailed on May 22, 2013, 7 pages.
Non-Final Office Action for U.S. Appl. No. 12/760,049, mailed Oct. 3, 2013, 19 pages.

* cited by examiner

US 9,011,489 B2

SURGICAL COMPOSITE BARBED SUTURE

CROSS-REFERENCE TO RELATED APPLICATION

This application claims priority to U.S. Provisional Patent Application Ser. No. 61/071,726, entitled "Surgical Composite Barbed Suture," filed May 14, 2008, the disclosure of which is incorporated herein by reference in its entirety.

BACKGROUND

This invention relates to a medical device and more particularly to a suture including multiple tissue anchors.

The disclosed embodiments have application to a wide variety of surgical procedures including those that require high anchoring strength. For example, one such procedure is directed to female urinary incontinence and involves insertion of a suture to be fixed to bodily tissue under and/or lateral to the urethra to reconstitute the ligamentary support for the urethra. Generally, the suture is inserted into two or more body tissues to couple the body tissues tightly together without knotting the suture.

A known suture device includes an elongated body and a plurality of axially and circumferentially spaced barbs formed on the exterior surface of the elongated body. Such sutures may be placed within a body of a patient approximate bodily tissue. During insertion, a suture may be uni-directionally adjusted with respect to each bodily tissue. Said another way, the suture may be inserted into bodily tissue in a first direction but is inhibited or prevented from moving in a second direction opposite the first direction.

For example, in using such a known suture in closing a wound with such a suture, the suture is passed through tissue at each of the opposed sides of the wound. Suture pairs are formed in which trailing ends of sutures are positioned generally in alignment at opposite sides of the wound. On insertion of each suture, the suture is pushed to extend out of the tissue at a point laterally remote from the wound and the suture is moved to the desired position.

The width of such known sutures is reduced when producing such sutures because the barbs are formed by the suture. Thus, the width of a prong is limited by the width of the suture. The process of reducing the width of the suture also disadvantageously reduces its tensile strength. Such sutures must also be sufficiently rigid such that the barbs can prevent movement in the second direction. In some applications, however, it is desirable or necessary to have a suture having a flexible filament with a high tensile strength and a small filament width as well as multiple large barbs.

Thus, a need exists for a medical device (e.g., a suture) having a flexible filament with a high tensile strength and a small filament width as well as multiple large barbs.

SUMMARY OF THE INVENTION

In one embodiment, a medical device includes an elongate member configured to be inserted into a body. The elongate member has a first end portion and a second end portion opposite the first end portion. The elongate member includes a retaining member extending from the elongate member. The retaining member is configured to anchor the elongate member with respect to bodily tissue. The first end portion of the elongate member includes a coupling portion configured to be coupled to a filament. The second end portion of the elongate member includes a coupling portion configured to be coupled to the filament.

In another embodiment, a medical device includes a first tissue anchor including a retaining member extending therefrom. The medical device includes a second tissue anchor including a retaining member extending therefrom. The medical device includes a filament coupled to the first tissue anchor and coupled to the second tissue anchor. The medical device is configured to be inserted into a body of a patient and configured to move in a first direction with respect to bodily tissue. The retaining member of the first tissue anchor and the retaining member of the second tissue anchor each are configured to help prevent the medical device from moving in a second direction with respect to the bodily tissue. The second direction is different from the first direction.

In yet another embodiment, a medical device includes a set of tissue anchors configured to anchor to bodily tissue. Each tissue anchor from the set of tissue anchors has a first end portion and a second end portion opposite the first end portion. The first end portion of each tissue anchor from the set of tissue anchors defines an opening. The second end portion of each tissue anchor from the set of tissue anchors defines an opening. Each tissue anchor from the set of tissue anchors defines a lumen extending from the first opening to the second opening. The medical device includes a filament that is coupled to the each tissue anchor from the set of tissue anchors and extends through the lumen of each tissue anchor from the set of tissue anchors.

BRIEF DESCRIPTION OF THE DRAWINGS

The invention is described with reference to the accompanying drawings.

DETAILED DESCRIPTION

The medical device described herein can be inserted into a body of a patient, such as within bodily tissue. For example, the medical device can be configured as a suture that can couple a first bodily tissue to a second bodily tissue. In some embodiments, the medical device can help provide support for a urethra or other anatomical structure. The medical device or suture includes multiple tissue anchors and a filament that is coupled to each of the tissue anchors. In some embodiments, the tissue anchors have the same orientation with respect to the filament when the filament is in a linear configuration. The suture can be inserted into bodily tissue in a first direction. The suture, however, is prevented from moving in a second direction different than the first direction due to the orientation and structure of the tissue anchors.

Figure 1:
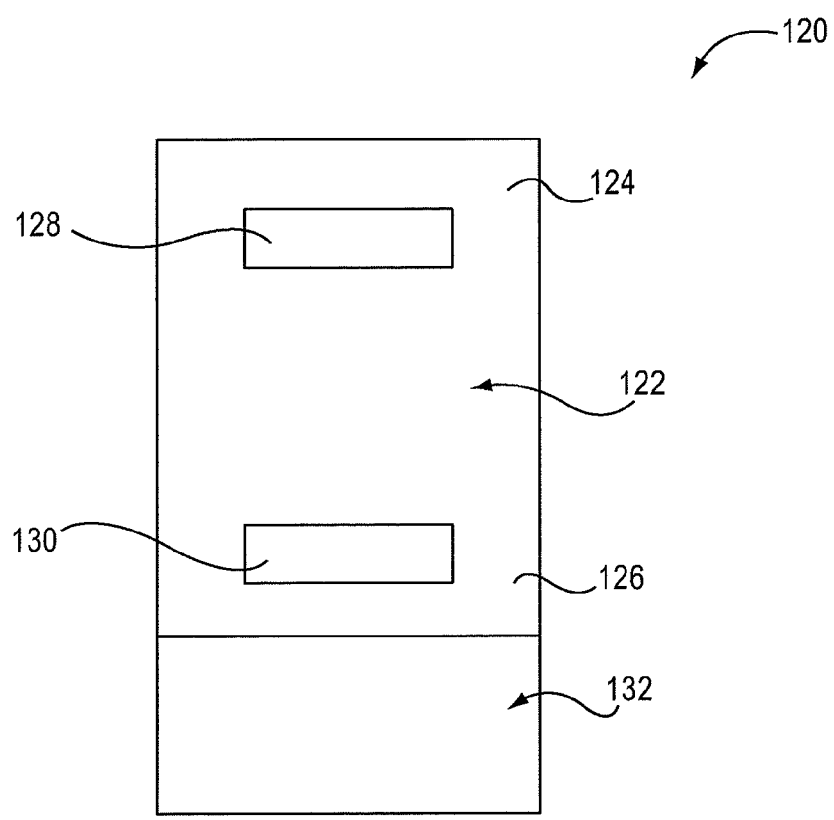
FIG. 1 is a schematic illustration of an anchor according to an embodiment of the invention.

FIG. 1 is a schematic illustration of a tissue anchor according to an embodiment of the invention. An apparatus 120 (also referred to herein as "tissue anchor") can be placed or otherwise inserted into a body of a patient, such as, for example, within a pelvic floor region of the body.

The tissue anchor 120 includes an elongate member 122 having a first end portion 246 and a second end portion 126 opposite the first end portion 124. The first end portion 124 of the elongate member 122 includes a coupling portion 128 that can be coupled to a filament (not shown). The second end portion 126 of the elongate member 122 includes a coupling portion 130. The coupling portion 130 of the second end portion 126 can be coupled to the filament. The elongate member 122 includes an anchoring portion 132 that can anchor the tissue anchor 120 with respect to bodily tissue when inserted into bodily tissue. In some embodiments, the first end portion of the elongate member includes the anchoring portion. In other embodiments, the second end portion of the elongate member includes the anchoring portion. In yet other embodiments, the first end portion and the second end portion of the elongate member each includes an anchoring portion.

In some embodiments, the anchoring portion 132 is a retaining member that extends from the elongate member 122. The retaining member can anchor the elongate member with respect to bodily tissue. The retaining member can be, for example, a barb, a prong, a tab, or the like. In some embodiments, the anchoring portion includes multiple retaining members extending from the elongate member. In some embodiments, the retaining members can flex or bend to facilitate insertion into bodily tissue. In other embodiments, the retaining members are rigid or do not bend.

In some embodiments, the first end portion defines an opening and the second end portion defines an opening. The elongate member defines a lumen extending from the opening of the first end portion to the opening of the second end portion. In such embodiments, the filament can extend through the lumen defined by the elongate member and be coupled to the tissue anchor via an interference fit. In other embodiments, the suture can include a second filament. In such embodiments, the elongate member can define a first lumen and second lumen separate from the first lumen. The first lumen can extend from the first opening and can be coupled to the first filament via an interference fit. Similarly, the second lumen can extend from the second opening and can couple to the second filament via an interference fit.

In some embodiments, the elongate member defines an opening having a first portion and a second portion different than the first portion. The coupling portion of the first end portion includes an inner wall of the first portion of the opening such that when the filament is coupled to the first end portion the filament engages the inner wall of the first portion of the opening. The coupling portion of the second end portion includes an inner wall of the second portion of the opening such that when the filament is coupled to the second end portion the filament engages the inner wall of the second portion of the opening. In some embodiments, the inner wall that defines the opening is disposed within at least one loop formed by the filament.

In some embodiments, the elongate member defines a first opening and a second opening where an inner wall of the first opening and an inner wall of the second opening engage the filament when the filament is coupled to the first end portion and the second end portion, respectively. Specifically, in some embodiments, the elongate member has a first side portion and a second side portion opposite the first side portion. The first end portion of the elongate member defines an opening that extends from the first side portion to the second side portion. The coupling portion of the first end portion includes an inner wall that defines the opening of the first end portion such that when the filament is coupled to the first end portion the filament engages the inner wall that defines the opening of the first end portion. Similarly, the second end portion of the elongate member defines an opening extending from the first side portion to the second side portion. The coupling portion of the second end portion includes an inner wall that defines the opening of the second end portion such that when the filament is coupled to the second end portion the filament engages the inner wall that defines the opening of the second end portion. In some embodiments, the elongate member defines a lumen extending from the opening of the first end portion to the opening of the second end portion. The lumen of the elongate member having a width sufficient for the filament to be disposed within the lumen. In other words, the lumen can receive the filament such that the filament extends from the opening of the first end portion to the opening of the second end portion.

In some embodiments, the filament is coupled to the elongate member via a knot. Specifically, the filament is coupled to the coupling portion of the first end portion via a knot formed by the filament at the coupling portion of the first end portion. Similarly, in some embodiments, the filament is coupled to the coupling portion of the second end portion via a knot formed by the filament at the coupling portion of the second end portion. In some embodiments, multiple knots can be at both the coupling portion of the first end portion and the coupling portion of the second end portion.

In some embodiments, the filament and the elongate member can be coupled via a molding of either the filament to the elongate member and/or the elongate member to the filament. For example, the filament is coupled to the coupling portion of the first end portion via a molding of the filament to the coupling portion of the first end portion.

In some embodiments, the filament is coupled to the elongate member via an adhesive, such as, for example, glue or the like. Specifically, the filament is coupled to the coupling portion of the first end portion via an adhesive between the filament and the coupling portion of the first end portion. Similarly, in some embodiments, the filament is coupled to the coupling portion of the second end portion via an adhesive between the filament and the coupling portion of the second end portion. In some embodiments, the filament is coupled to the coupling portion of the second end portion via a knot and an adhesive at the knot between the filament and the coupling portion of the second end portion.

Figure 2:
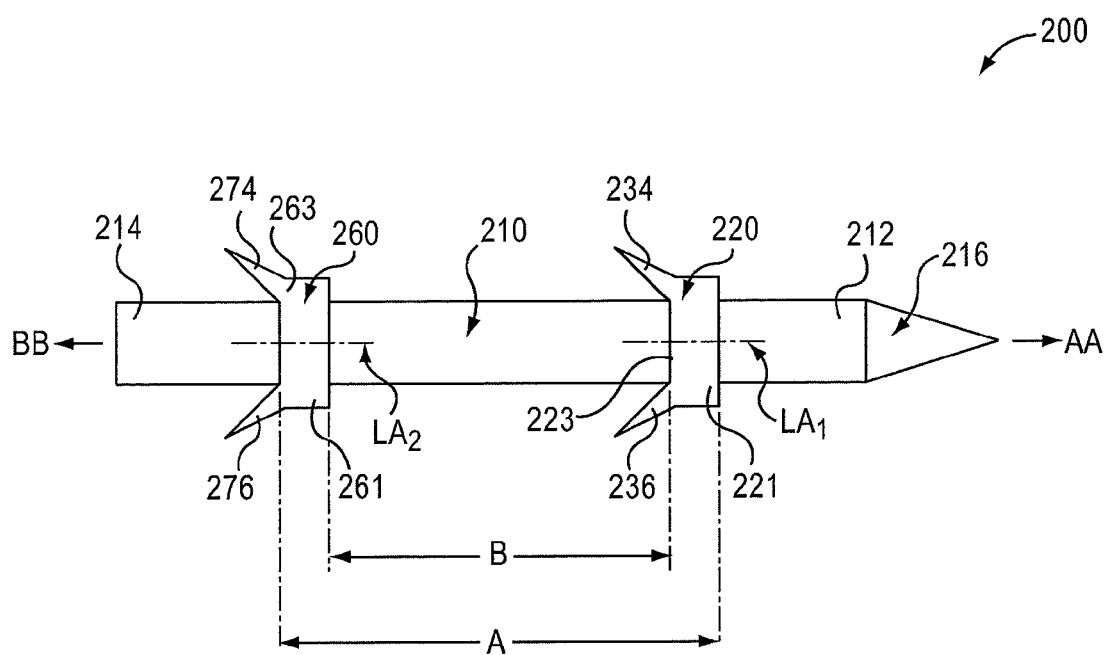
FIG. 2 is a schematic illustration of a medical device according to an embodiment of the invention.

FIG. 2 is a schematic illustration of a medical device according to an embodiment. The suture 200 includes a first tissue anchor 220, a second tissue anchor 260 and a filament 210. The first tissue anchor 220 has a first end portion 221 and a second end portion 223 opposite the first end portion 221. The second tissue anchor 260 has a first end portion 261 and a second end portion 263 opposite the first end portion 261. The filament 210 has a first end portion 212 and a second end portion 214 opposite the first end portion 212.

The filament 210 is coupled to the first tissue anchor 220 and the second tissue anchor 260. In some embodiments, the filament 210 is coupled to the first end portion 221 of the first tissue anchor 220, coupled to the second end portion 223 of the first tissue anchor 220, coupled to the first end portion 261 of the second tissue anchor 260 and coupled to the second end portion 263 of the second tissue anchor 260.

After the suture 200 is inserted into a body of a patient, the suture 200 can move in a first direction AA with respect to bodily tissue. In some embodiments, the suture 200 includes a needle 216 coupled to the first end portion 212 of the filament 210. The needle 216 is rigid and can pierce bodily tissue. In the illustrated embodiment, the needle 216 is substantially conical in shape. In an alternative embodiment, the needle is substantially frusto-conical in shape.

After the suture 200 is inserted into the body of the patient, the suture 200 resists movement in a second direction BB different than the first direction AA. Specifically, the second end portion 223 of the first tissue anchor 220 includes a first retaining member 234 and a second retaining member 236 extending from the first tissue anchor 220. Similarly, the second end portion 263 of the second tissue anchor 260 includes a first retaining member 274 and a second retaining member 276 extending from the second tissue anchor 260. The retaining members 234, 236, 274 and 276 are each configured to help prevent the suture 200 from moving in the second direction with respect to the bodily tissue. More specifically, the retaining members 234 and 236 of the first tissue anchor 220 extend angularly away from a longitudinal axis $LA_1$ defined by the first tissue anchor 220 and towards the second end portion 214 of the filament 210 (e.g., away from the first end portion 221 of the first tissue anchor 220) when the filament 210 is in a linear configuration. Similarly, the retaining members 274 and 276 of the second tissue anchor 260 extend angularly away from a longitudinal axis $LA_2$ defined by the second tissue anchor 260 and towards the second end portion 214 of the filament 210 (e.g., away from the first end portion 261 of the second tissue anchor 260) when the filament 210 is in its linear configuration. Said another way, the retention members 234, 236, 274 and 276 of the tissue anchors 220 and 260 each extend from the longitudinal axes $LA_1$ and $LA_2$ defined by their respective tissue anchors 220 and 260 and towards the second end portion 214 of the filament 210 when the filament 210 is in a linear configuration. The retaining members 234, 236, 274 and 276 can be, for example, barbs, prongs, etc.

In the illustrated embodiment, the first end portion 221 of the first tissue anchor 220 is separated by a first distance A from the second end portion 263 of the second tissue anchor 260. Similarly, the second end portion 223 of the first tissue anchor 220 is separated by a second distance B from the first end portion 261 of the second tissue anchor 260. The first distance A is greater than the second distance B. Said another way, the tissue anchors 220 and 260 have the same orientation with respect to the filament 210 when the filament 210 is its linear configuration.

In some embodiments, more than two tissue anchors can be coupled to the filament. For example, in some embodiments, the suture includes a third tissue anchor that includes a retaining member extending therefrom. The third tissue anchor has a first end portion and a second end portion opposite the first end portion. The filament is coupled to the first end portion of the third filament and is coupled to the second end portion of the third tissue anchor.

In some embodiments, the filament is flexible. Said another way, the first end portion of the filament can bend or turn with respect to the second end portion of the filament.

Figure 3:
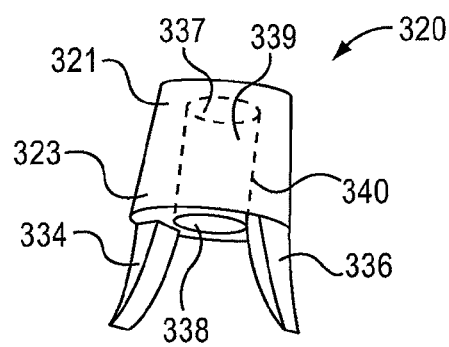
FIG. 3 is a perspective view of an anchor according to an embodiment of the invention.
Figure 4:
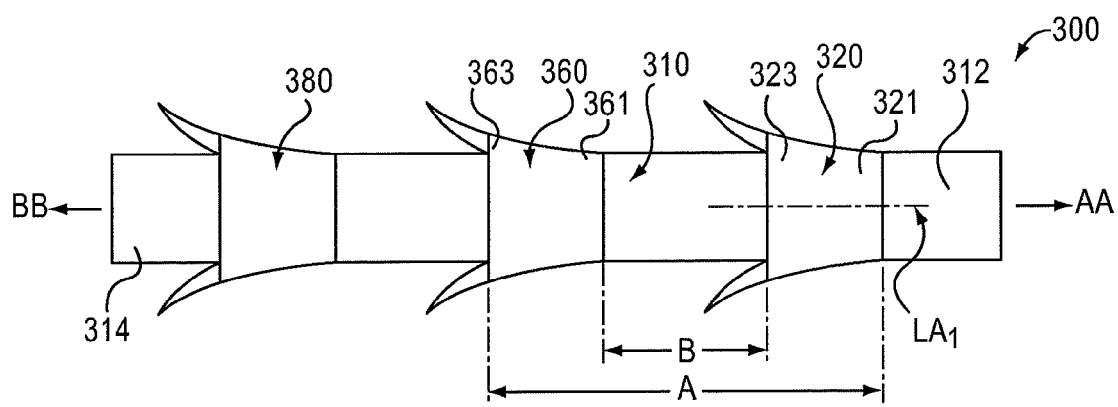
FIG. 4 is a side view of a medical device including the anchor of FIG. 3.

FIG. 3 is a perspective view of an anchor according to an embodiment of the invention. FIG. 4 is a side view of a medical device including the anchor of FIG. 3. The medical device or suture 300 includes a filament 310, a first tissue anchors 320, a second tissue anchor 360 and a third tissue anchor 380. The filament 310 has a first end portion 312 and a second end portion 314 opposite the first end portion 312.

Although multiple tissue anchors 320, 360 and 380 are illustrated in FIG. 4, only the first tissue anchor 320 will be described in detail. The other tissue anchors 360 and 380 are each structurally and functionally similar to the first tissue anchor 320.

The first tissue anchor 320 has a first end portion 321 and a second end portion 323 opposite the first end portion 321. The term "tissue anchor" is used herein for convenience. The term "tissue anchor" can be synonymous with an "elongate member." Accordingly, the first end portion 321 of the first tissue anchor 320 can also be referred to as a first end portion of the elongate member. Similarly, the second end portion 323 of the first tissue anchor 320 can also be referred to as a second end portion of the elongate member.

As shown in FIG. 3, the first end portion 321 of the first tissue anchor 320 defines an opening 337 and the second end portion 323 of the first tissue anchor 320 defines an opening 338. The first tissue anchor 320 defines a lumen 339 extending from the opening 337 of the first end portion 321 of the first tissue anchor 320 to the opening 338 of the second end portion 323 of the first tissue anchor 320. As shown in FIG. 4, the filament 310 is coupled to the first tissue anchor 320. Specifically, the filament 310 disposed within the lumen 339 and is coupled to the first tissue anchor 320 via an interference fit. Said another way, an inner wall 340 of the lumen 339 contacts the filament 310 such that the inner wall 340 of the lumen 339 imparts a frictional force on the filament 310 sufficient to anchor at a fixed location along the filament 310.

After the suture 300 is inserted into the bodily tissue, the suture 300 can move in a first direction AA with respect to the bodily tissue. The suture 300 can include a needle (not shown) coupled to the first end portion 312 of the filament 310. The needle can be rigid and can be configured to pierce bodily tissue.

After the suture 300 is inserted into the bodily tissue, the suture 300 resists movement in a second direction BB different than the first direction AA. For example, the second direction BB can be opposite the first direction AA. Specifically, the second end portion 323 of the first tissue anchor 320 includes a retaining portion that has multiple retaining members 334 and 336 extending therefrom. More specifically, the first tissue anchor 320 includes a first retaining member 334 and a second retaining member 336. The first retaining member 334 and the second retaining member 336 can help anchor the first tissue anchor 320 with respect to bodily tissue when the suture 300 is inserted into the bodily tissue. Said differently, the first retaining member 334 and the second retaining member 336 are each configured to help prevent the suture 300 from moving in the second direction BB with respect to the bodily tissue. The retaining members 334 and 336 can be, for example, a barb, a prong, a tab, or the like. In some embodiments, the first end portion of the first tissue anchor includes the retaining members instead of the second end portion. In other embodiments, the first end portion of the first tissue anchor includes another retaining member.

In the illustrated embodiment, the retaining members 334 and 336 of the first tissue anchor 320 extend angularly away from a longitudinal axis $LA_1$ defined by the first tissue anchor 320 and towards the second end portion 314 of the filament 310 (e.g., away from the first end portion 321 of the first tissue anchor 320) when the filament 310 is in a linear configuration. Said another way, the retention members 334 and 336 of the first tissue anchor 320 extend from the longitudinal axis $LA_1$ defined by the first tissue anchor 320 and towards the second end portion 314 of the filament 310 when the filament 310 is in a linear configuration.

During insertion of the suture 300 into bodily tissue, the bodily tissue moves with respect to or is displaced by at least a portion of the first tissue anchor 320. The bodily tissue can then prolapse back with respect to the retaining members 334 and 336 anchoring the first tissue anchor 320 with respect to the bodily tissue. Although in this embodiment, the first tissue anchor 320 is anchored with respect to the bodily tissue via multiple retention members 334 and 336, it should be understood that any retaining or anchoring mechanism can be used, such as, for example, a balloon, a screw, etc. In some embodiments, more or less than two retention members can be used.

In the illustrated embodiment, the first end portion 321 of the first tissue anchor 320 is separated by a first distance A from the second end portion 363 of the second tissue anchor 360. Similarly, the second end portion 323 of the first tissue anchor 320 is separated by a second distance B from the first end portion 361 of the second tissue anchor 360. The first distance A is greater than the second distance B.

In some embodiments, the medical includes a second filament. In some embodiments, for example, the first tissue anchor defines a first lumen and second lumen separate from the first lumen. The first lumen can extend from the first opening and receive the first filament such that the first filament is coupled to first the lumen via an interference fit. Similarly, the second lumen can extend from the second opening and receive the second filament such that the second filament is coupled to the second lumen via an interference fit.

In some embodiments, the filament is flexible. Said another way, the first end portion of the filament can bend or turn with respect to the second end portion of the filament.

In some embodiments, the second tissue anchor and the third tissue anchor are a different type of anchor than the first tissue anchor. In other words, the second tissue anchor and the third tissue anchor do have similar structure and/or functions as the first tissue anchor.

Figure 5:
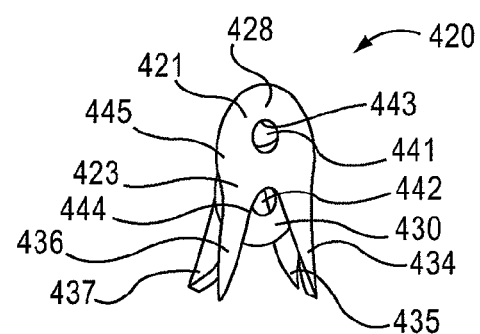
FIG. 5 is a perspective view of an anchor according to an embodiment of the invention.
Figure 6:
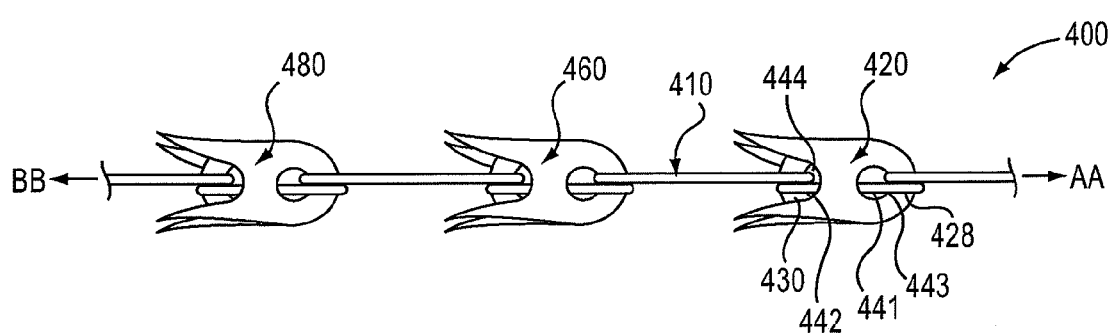
FIG. 6 is a side view of a medical device including the anchor of FIG. 5.

FIG. 5 is a perspective view of an anchor according to an embodiment of the invention. FIG. 6 is a side view of a medical device including anchor of FIG. 5. The suture 400 includes a filament 410 and a first tissue anchor 420, a second tissue anchor 460 and a third tissue anchor 480.

Although multiple tissue anchors 420 and 460 are illustrated in FIG. 6, only the first tissue anchor 420 will be described in detail. The other tissue anchors 460 and 480 are each structurally and functionally similar to the first tissue anchor 420 and includes similar components. In some embodiments, another tissue anchor is different from the first tissue anchor and has different components.

The first tissue anchor 420 has a first end portion 421 and a second end portion 423 opposite the first end portion 421. As shown in FIG. 6, the first end portion 421 of the first tissue anchor 420 includes a coupling portion 428 coupled to the filament 410. The second end portion 423 of the first tissue anchor 420 includes a coupling portion 430 coupled to the filament 410. Specifically, the first tissue anchor 420 has a first side portion 445 and a second side portion (not shown) opposite the first side portion 445. The first tissue anchor 420 defines a first opening 441 that extends from the first side portion 445 to the second side portion. The coupling portion 428 of the first end portion 421 includes the inner wall 443 of the first opening 441 of the first end portion 421 such that when the filament 410 is coupled to the first end portion 421 the filament 410 engages the inner wall 443 of the first opening 441 of the first end portion 421 as shown in FIG. 6. Similarly, the first tissue anchor 420 defines a second opening 442 that extends from the first side portion 445 to the second side portion. The coupling portion 430 of the second end portion 423 includes an inner wall 444 of the second opening 442 of the second end portion 423 such that when the filament 410 is coupled to the second end portion 423 the filament 410 engages the inner wall 444 of the second opening 442 of the second end portion 423 as shown in FIG. 6.

As shown in FIG. 6, the filament 410 is coupled to the first end portion 421 and the second end portion 423 via a knot. Specifically, a portion of the inner wall 443 of the first opening 441 is disposed within a first loop formed by the filament 410. Similarly, a portion of the inner wall 444 of the second opening 442 is disposed within a second loop formed by the filament 410. In some embodiments, the filament 410 can form more or less than two loops.

Similar to the above embodiment, after the suture 400 is inserted into the body of the patient, the suture 400 resists movement in a second direction BB opposite a first direction AA. Specifically, the second end portion 423 of the first tissue anchor 420 includes multiple retaining members 434, 435, 436 and 437 extending from the first tissue anchor 420. The retaining members 434, 435, 436 and 437 are each configured to help prevent the suture 400 from moving in the second direction BB with respect to bodily tissue.

In some embodiments, the first tissue anchor defines a lumen extending from the opening of the first end portion to the opening of the second end portion. The lumen of the elongate member having a width sufficient for the filament to be disposed within the lumen. In other words, the lumen can receive the filament such that the filament 410 extends from the opening of the first end portion to the opening of the second end portion.

Figure 7:
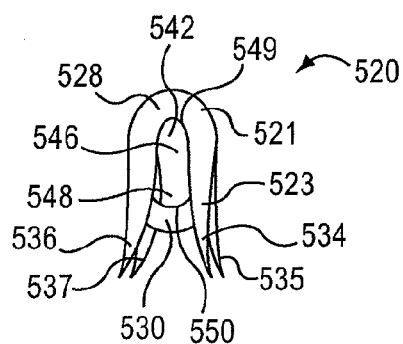
FIG. 7 is a perspective view of an anchor according to an embodiment of the invention.
Figure 8:
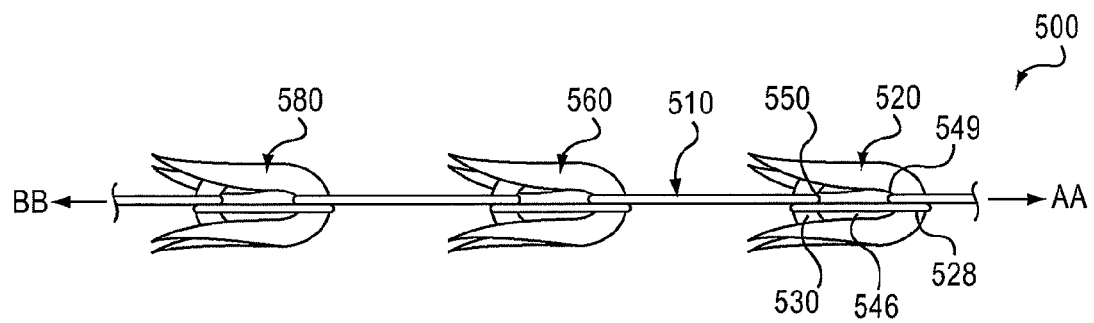
FIG. 8 is a side view of a medical device including the anchor of FIG. 7.

FIG. 7 is a perspective view of an anchor according to an embodiment of the invention. FIG. 8 is a side view of a medical device including the portion of the medical device of FIG. 7. The suture 500 includes a filament 510 and a first tissue anchor 520, a second tissue anchor 560 and a third tissue anchor 580. The first tissue anchor 520 includes a first end portion 521 and a second end portion 523 opposite the first end portion 521.

Although multiple tissue anchors 520 and 560 are illustrated in FIG. 8, only the first tissue anchor 520 will be described in detail. The other tissue anchors 560 are each a duplicate of the first tissue anchor 520 and includes similar components.

As shown in FIG. 8, similar to the above embodiments, the first end portion 521 of the first tissue anchor 520 includes a coupling portion 528 coupled to the filament 510. The second end portion 523 of the first tissue anchor 520 includes a coupling portion 530 coupled to the filament 510. Specifically, the first tissue anchor 520 defines an opening 446 that has a first portion 547 and a second portion 548. The coupling portion 528 of the first end portion 521 includes the inner wall 549 that defines the first portion 547 of the opening 546 such that when the filament 510 is coupled to the first end portion 521 the filament 510 engages the inner wall 549. Similarly, the coupling portion 530 of the second end portion 523 includes an inner wall 550 that defines the second portion 548 of the opening 546 such that when the filament 510 is coupled to the second end portion 523 the filament 510 engages the inner wall 550 of the second portion 548 of the opening 546.

As shown in FIG. 8, the filament 510 is coupled to the first end portion 521 and the second end portion 523 via a knot. Specifically, a portion of the inner wall 549 of the first portion 547 of the opening 546 is disposed within a first loop formed by the filament 510. Similarly, a portion of the inner wall 550 of the second portion 548 of the opening 546 is disposed within a second loop formed by the filament 510. In some embodiments, the filament 510 can form more or less than two loops.

Similar to the above embodiments, after the suture 500 is inserted into the body of the patient, the suture 500 resists movement in a second direction BB opposite a first direction AA. Specifically, the second end portion 523 of the first tissue anchor 520 includes multiple retaining members 534, 535, 536 and 537 extending from the first tissue anchor 520. The retaining members 534, 535, 536 and 537 are each configured to help prevent the suture 500 from moving in the second direction BB with respect to bodily tissue.

The tissue anchors can be made of any material known in the art of tissue anchors, including for example, biocompatible polymers, metals, or the like. In some embodiments, the first and/or second tissue anchor includes an opaque material. The filament can be made of any material known in the art of filaments. For example, the filament can be a monofilament suture, a braided suture, a tape, a mesh, or include a mesh-like material.

In some embodiments, a first suture is inserted into a first bodily tissue and a second bodily tissue in a first direction and a second suture is inserted into the first bodily tissue and the second bodily tissue in a second direction different than the first direction to approximate the first bodily tissue and the second bodily tissue. In some embodiments, a suture is inserted into a first bodily tissue and a second bodily tissue in a first direction. The suture can bend such that a portion of the suture can be moved through the first bodily tissue and the second bodily tissue in a second direction different than the first direction to approximate the first bodily tissue and the second bodily tissue.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The previous description of the embodiments is provided to enable any person skilled in the art to make and use the invention. While the invention has been particularly shown and described with reference to embodiments thereof, it will be understood by those skilled in the art that various changes in form and details may be made. For example, a suture can include various combinations and sub-combinations of the various embodiments described herein. For example, in some embodiment, various anchoring mechanisms can be used on a tissue anchor. In some embodiments, a tissue anchor can have two or more different coupling means. For example, a first end portion of a tissue anchor can include an inner wall that defines an opening such that a filament can be coupled to it via a knot and glue between the knot and the inner wall of the first end portion. The second end portion of the tissue anchor can include an inner wall that defines a lumen such that the filament is coupled to the inner wall of the second end portion via an interference fit.

In one embodiment, a tissue anchor includes an elongate member configured to be inserted into a body. The elongate member has a first end portion and a second end portion opposite the first end portion. The elongate member includes a retaining member that extends from the elongate member. The retaining member is configured to anchor the elongate member with respect to bodily tissue. The first end portion of the elongate member includes a coupling portion configured to be coupled to a filament. The second end portion of the elongate member includes a coupling portion configured to be coupled to the filament.

In some embodiments, the first end portion defines an opening. The second end portion defines an opening. The elongate member defines a lumen extending from the opening of the first end portion to the opening of the second end portion. The lumen is configured to be coupled to the filament within the lumen by interference fit.

In some embodiments, the elongate member defines an opening having a first portion and a second portion different than the first portion. The coupling portion of the first end portion includes an inner wall that defines the first portion of the opening such that when the filament is coupled to the first end portion the filament engages the inner wall of the coupling portion of the first end portion. The coupling portion of the second end portion includes an inner wall that defines the second portion of the opening such that when the filament is coupled to the second end portion the filament engages the inner wall of the coupling portion of the second end portion.

In some embodiments, the first end portion of the elongate member defines an opening. The coupling portion of the first end portion includes an inner wall that defines the opening of the first end portion. When the filament is coupled to the first end portion the filament engages the inner wall that defines the opening of the first end portion. The second end portion of the elongate member defines an opening. The coupling portion of the second end portion includes an inner wall that defines the opening of the second end portion. When the filament is coupled to the second end portion the filament engages the inner wall that defines the opening of the second end portion.

In some embodiments, the elongate member has a first side portion and a second side portion opposite the first side portion. The first end portion of the elongate member defines an opening extending from the first side portion to the second side portion. The coupling portion of the first end portion includes an inner wall that defines the opening of the first end portion such that when the filament is coupled to the first end portion the filament engages the inner wall that defines the opening of the first end portion. The second end portion of the elongate member defines an opening extending from the first side portion to the second side portion. The coupling portion of the second end portion includes an inner wall that defines the opening of the second end portion such that when the filament is coupled to the second end portion the filament engages the inner wall that defines the opening of the second end portion. The elongate member defines a lumen extending from the opening of the first end portion to the opening of the second end portion. The lumen of the elongate member is configured to receive the filament.

In some embodiments, the filament is coupled to the coupling portion of the first end portion via a knot formed by the filament at the coupling portion of the first end portion. In some embodiments, the filament is coupled to the coupling portion of the first end portion via a molding of the filament to the coupling portion of the first end portion. In some embodiments, the filament is coupled to the coupling portion of the first end portion via an adhesive.

In another embodiment, a medical device includes a first tissue anchor including a retaining member extending therefrom. The medical device includes a second tissue anchor including a retaining member extending therefrom. The medical device includes a filament coupled to the first tissue anchor and coupled to the second tissue anchor. The medical device is configured to be inserted into a body of a patient and configured to move in a first direction with respect to bodily tissue. The retaining member of the first tissue anchor and the retaining member of the second tissue anchor are each configured to help prevent the medical device from moving in a second direction with respect to the bodily tissue. The second direction is different from the first direction.

In some embodiments, the first tissue anchor has a first end portion and a second end portion opposite the first end portion. The filament is coupled to the first end portion and coupled to the second end portion. The second tissue anchor has a first end portion and a second end portion opposite the first end portion. The filament is coupled to the first end portion of the second tissue anchor and coupled to the second end portion of the second tissue anchor.

In some embodiments, the filament has a first end portion and a second end portion opposite the first end portion. The retaining member of the first tissue anchor extends away from a longitudinal axis defined by the first tissue anchor and towards the second end portion of the filament when the filament is in a linear configuration. The retaining member of the second tissue anchor extends away from a longitudinal axis defined by the second tissue anchor and towards the second end portion of the filament when the filament is in its linear configuration.

In some embodiments, the first tissue anchor has a first end portion and a second end portion opposite the first end portion. The retaining member of the first tissue anchor extends away from a longitudinal axis defined by the first tissue anchor and extends away from the first end portion of the first tissue anchor. The second tissue anchor has a first end portion and a second end portion opposite the first end portion. The retaining member of the second tissue anchor extends away from a longitudinal axis defined by the second tissue anchor and extends away from the first end portion of the second tissue anchor. The first end portion of the first tissue anchor is separated by a first distance from the second end portion of the second tissue anchor. The second end portion of the first tissue anchor is separated by a second distance from the first end portion of the second tissue anchor. The second distance is greater than the first distance.

In some embodiments, the medical device includes a third tissue anchor including a retaining member extending therefrom. The third tissue anchor has a first end portion and a second end portion opposite the first end portion. The filament is coupled to the first end portion of the third tissue anchor and coupled to the second end portion of the third tissue anchor.

In some embodiments, the first tissue anchor defines a lumen therethrough. The first tissue anchor is coupled to the filament via an interference fit.

In some embodiments, the first tissue anchor defines an opening having an inner wall. A portion of the inner wall is disposed within at least one loop formed by the filament.

In some embodiments, the first tissue anchor defines a first opening including an inner wall. A portion of the inner wall that defines the first opening is disposed within a first at least one loop formed by the filament. The first tissue anchor defines a second opening different than the first opening. The second opening has an inner wall. A portion of the inner wall that defines the second opening is disposed within a second at least one loop formed by the filament.

In some embodiments, the first tissue anchor defines a first opening including an inner wall. A portion of the inner wall that defines the first opening is disposed within a first at least one loop formed by the filament. The first tissue anchor defines a second opening different than the first opening. The second opening has an inner wall. A portion of the inner wall that defines the second opening is disposed within a second at least one loop formed by the filament. The first tissue anchor defines a lumen extending from the first opening to the second opening. The lumen is configured to receive the filament.

In some embodiments, the filament is flexible.

In yet another embodiment, a medical device includes a set of tissue anchors configured to anchor to bodily tissue. The medical device is movable in a first direction and not in a second direction when a portion of the medical device is disposed in the bodily tissue. The second direction is opposite the first direction. Each tissue anchor from the set of tissue anchors has a first end portion and a second end portion opposite the first end portion. The first end portion of each tissue anchor from the set of tissue anchors defines an opening. The second end portion of each tissue anchor from the set of tissue anchors defines an opening. Each tissue anchor from the set of tissue anchors defines a lumen extending from the first opening to the second opening. The medical device includes a filament that is coupled to the each tissue anchor from the set of tissue anchors and extends through the lumen of each tissue anchor from the set of tissue anchors.

In some embodiments, a tissue anchor from the set of tissue anchors includes a retaining member extending angularly away from the tissue anchor such that the tissue anchor from the set of tissue anchors prevents movement of the medical device in at least one direction when a portion of the medical device is disposed in the bodily tissue.

In some embodiments, the filament has a first end portion and a second end portion opposite the first end portion. Each tissue anchor from the set of tissue anchors includes a retaining member extending away from a longitudinal axis defined by each respective tissue anchor from the set of tissue anchors and towards the second end portion of the filament when the filament is in a linear configuration.

In some embodiments, each tissue anchor from the set of tissue anchor is oriented in the same direction with respect to the filament when the filament is in a linear configuration.

In some embodiments, a tissue anchor from the set of tissue anchor includes a first barb angularly extending away from the first end portion of that tissue anchor. The tissue anchor from the set of tissue anchors includes a second barb angularly extending away from the first end portion of that tissue anchor. The first barb and the second barb each are configured to anchor the tissue anchor from the set of tissue anchors with respect to the bodily tissue.

In some embodiments, the filament is flexible. In some embodiments, the filament is coupled to the lumen via an interference fit.

What is claimed is:

1. A tissue anchor, comprising:
   an elongate member configured to be inserted into a body, the elongate member having a first end portion and a second end portion opposite the first end portion, the elongate member defining a longitudinal axis, the elongate member including a retaining member extending from the elongate member, the retaining member extending from the second end portion and being configured to anchor the elongate member with respect to bodily tissue,
   the first end portion of the elongate member including a coupling portion defining an opening having an axis, the axis of the opening and the longitudinal axis of the elongate member forming an angle, the coupling portion being configured to be coupled to a filament, the coupling portion of the first end portion being disposed on the longitudinal axis of the elongate member,
   the second end portion of the elongate member including a coupling portion configured to be coupled to the filament, the coupling portion of the second end portion being disposed on the longitudinal axis of the elongate member, the elongate member defining a lumen extending from the coupling portion of the first end portion to the coupling portion of the second end portion,
   wherein the coupling portion of the first end portion couples the filament via a first loop formed by the filament around the first end portion such that the first loop encircles the first end portion, and the coupling portion of the second end portion couples the filament via a second loop formed by the filament around the second end portion such that the second loop encircles the second end portion, the filament extending through the lumen of the elongate member along the longitudinal axis from the first loop to the second loop.

2. The tissue anchor of claim 1, wherein:
the coupling portion of the first end portion including an inner wall that defines the opening of the first end portion, when the filament is coupled to the first end portion the filament engages the inner wall that defines the opening of the first end portion,
the second end portion of the elongate member defines an opening, the coupling portion of the second end portion including an inner wall that defines the opening of the second end portion, when the filament is coupled to the second end portion the filament engages the inner wall that defines the opening of the second end portion, the lumen of the elongate member extending along the longitudinal axis from the inner wall of the first end portion to the inner wall of the second end portion.

3. The tissue anchor of claim 1, wherein:
the elongate member has a first side portion and a second side portion opposite the first side portion,
the opening of the first end portion extending from the first side portion to the second side portion, the coupling portion of the first end portion including an inner wall that defines the opening of the first end portion such that when the filament is coupled to the first end portion the filament engages the inner wall that defines the opening of the first end portion,
the second end portion of the elongate member defines an opening extending from the first side portion to the second side portion, the coupling portion of the second end portion including an inner wall that defines the opening of the second end portion such that when the filament is coupled to the second end portion the filament engages the inner wall that defines the opening of the second end portion, the lumen of the elongate member extending along the longitudinal axis from the inner wall of the first end portion to the inner wall of the second end portion.

4. The tissue anchor of claim 1, wherein the second end portion has an inner edge defining an opening, and the first end portion has an inner edge defining the opening of the first end portion, the lumen extending along the longitudinal axis from the inner edge of the first end portion to the inner edge of the second end portion.

5. The tissue anchor of claim 1, wherein the axis of the opening is disposed substantially perpendicular to the longitudinal axis.

6. The tissue anchor of claim 1, wherein the elongated member is configured to be inserted into the body in a first direction such that the retaining member prevents movement of the elongated member in a second direction opposite to the first direction, and the second end portion trails the first end portion with respect to the first direction such that the retaining member extending from the second end portion prevents movement in the second direction.

7. A medical device, comprising:
a first tissue anchor including a retaining member extending therefrom, the first tissue anchor defining a longitudinal axis, the first tissue anchor defining an opening having an axis, the axis of the opening and the longitudinal axis of the first tissue anchor forming an angle, the opening being disposed on the longitudinal axis of the first tissue anchor, the first tissue anchor including a first end portion and a second end portion, the first tissue anchor defining a lumen extending from the first end portion to the second end portion;
a second tissue anchor including a retaining member extending therefrom, the second tissue anchor including a first end portion and a second end portion; and
a filament being coupled to the first end portion of the first tissue anchor via a first loop formed by the filament around the first end portion of the first tissue anchor such that the first loop encircles the first end portion of the first tissue anchor, the filament being coupled to the second end portion of the first tissue anchor via a second loop formed by the filament around the second end portion of the first tissue anchor such that the second loop encircles the second end portion of the first tissue anchor, the filament extending through the lumen of the first tissue anchor along the longitudinal axis from the first loop to the second loop,
the filament being coupled to the first end portion of the second tissue anchor via a third loop formed by the filament around the first end portion of the second tissue anchor such that the third loop encircles the first end portion of the second tissue anchor, the filament being coupled to the second end portion of the second tissue anchor via a fourth loop formed by the filament around the second end portion of the second tissue anchor such that the fourth loop encircles the second end portion of the second tissue anchor,
the medical device being configured to be inserted into a body of a patient and configured to move in a first direction with respect to bodily tissue, the retaining member of the first tissue anchor and the retaining member of the second tissue anchor each configured to help prevent the medical device from moving in a second direction with respect to the bodily tissue, the second direction being different from the first direction, the retaining member of the first tissue anchor extending away from the second end portion of the first tissue anchor, the retaining member of the second tissue anchor extending away from the second end portion of the second tissue anchor.

8. The medical device of claim 7, wherein:
the filament has a first end portion and a second end portion opposite the first end portion,
the retaining member of the first tissue anchor extending away from the longitudinal axis defined by the first tissue anchor and towards the second end portion of the filament when the filament is in a linear configuration,
the retaining member of the second tissue anchor extending away from a longitudinal axis defined by the second tissue anchor and towards the second end portion of the filament when the filament is in its linear configuration.

9. The medical device of claim 7, wherein:
the retaining member of the first tissue anchor extending away from the longitudinal axis defined by the first tissue anchor,
the retaining member of the second tissue anchor extending away from a longitudinal axis defined by the second tissue anchor,
the first end portion of the first tissue anchor being separated by a first distance from the second end portion of the second tissue anchor,
the second end portion of the first tissue anchor being separated by a second distance from the first end portion of the second tissue anchor, the second distance being greater than the first distance.

10. The medical device of claim 7, further comprising:
a third tissue anchor including a retaining member extending therefrom, the third tissue anchor having a first end portion and a second end portion opposite the first end portion, the filament being coupled to the first end portion of the third tissue anchor via a fifth loop formed by the filament around the first end portion of the third tissue anchor such that the fifth loop encircles the first end portion of the third tissue anchor, the filament being coupled to the second end portion of the third tissue anchor via a sixth loop formed by the filament around the second end portion of the third tissue anchor such that the sixth loop encircles the second end portion of the third tissue anchor.

11. The medical device of claim 7, wherein the opening of the first tissue anchor has an inner wall, a first portion of the inner wall being disposed within the first loop formed by the filament around the first end portion of the first tissue anchor, a second portion of the inner wall being disposed within the second loop formed by the filament around the second end portion of the first tissue anchor.

12. The medical device of claim 7, the opening of the first tissue anchor being a first opening of the first tissue anchor, wherein:
the first opening of the first tissue anchor includes an inner wall, a portion of the inner wall of the first opening being disposed within the first loop formed by the filament around the first end portion of the first tissue anchor,
the first tissue anchor defines a second opening, the second opening having an inner wall, a portion of the inner wall of the second opening being disposed within the second loop formed by the filament around the second end portion of the first tissue anchor, the lumen of the first tissue anchor extending from the inner wall defined by the first opening to the inner wall defined by the second opening.

13. The medical device of claim 7, the opening of the first tissue anchor being a first opening of the first tissue anchor, wherein:
the first opening of the first tissue anchor includes an inner wall, a portion of the inner wall of the first opening being disposed within the first loop formed by the filament around the first end portion of the first tissue anchor,
the first tissue anchor defines a second opening different than the first opening, the second opening having an inner wall, a portion of the inner wall of the second opening being disposed within the second loop formed by the filament around the second end portion of the first tissue anchor,
the first tissue anchor defines a lumen extending from the first opening to the second opening, the lumen being configured to receive the filament.

14. The medical device of claim 7, wherein the filament is flexible.

15. A medical device, comprising:
a plurality of tissue anchors configured to anchor to bodily tissue, the medical device being movable in a first direction and not in a second direction when a portion of the medical device is disposed in the bodily tissue, the second direction being opposite the first direction, each tissue anchor from the plurality of tissue anchors defining a longitudinal axis and having a first end portion and a second end portion opposite the first end portion, the first end portion of each tissue anchor from the plurality of tissue anchors defining an opening having an axis disposed at an angle with respect to the longitudinal axis, the second end portion of each tissue anchor from the plurality of tissue anchors defining an opening, each tissue anchor from the plurality of tissue anchors defining a lumen extending from the first end portion to the second end portion such that the opening defined by the first end portion extends to the opening defined by the second end portion along the longitudinal axis, the first opening and the second opening of each of the plurality to tissue anchors being disposed on the longitudinal axis of each of the plurality of tissue anchors; and
a filament being coupled to the each tissue anchor from the plurality of tissue anchors and extending through the lumen of each tissue anchor from the plurality of tissue anchors,
wherein the filament is coupled to the first end portion of each tissue anchor via a first loop formed by the filament around the first end portion of each tissue anchor such that the first loop encircles the first end portion of each tissue anchor, and the filament is coupled to the second end portion of each tissue anchor via a second loop formed by the filament around the second end portion of each tissue anchor such that the second loop encircles the second end portion of each tissue anchor, the filament extending through the lumen of each tissue anchor along the longitudinal axis from the first loop to the second loop.

16. The medical device of claim 15, wherein a tissue anchor from the plurality of tissue anchors includes a retaining member extending angularly away from the tissue anchor such that the tissue anchor from the plurality of tissue anchors prevents movement of the medical device in at least one direction when a portion of the medical device is disposed in the bodily tissue.

17. The medical device of claim 15, wherein:
the filament has a first end portion and a second end portion opposite the first end portion, each tissue anchor from the plurality of tissue anchors including a retaining member extending away from a longitudinal axis defined by each respective tissue anchor from the plurality of tissue anchors and towards the second end portion of the filament when the filament is in a linear configuration.

18. The medical device of claim 15, wherein each tissue anchor from the plurality of tissue anchor is oriented in the same direction with respect to the filament when the filament is in a linear configuration.

19. The medical device of claim 15, wherein a tissue anchor from the plurality of tissue anchor includes a first barb angularly extending away from the first end portion of that tissue anchor, the tissue anchor from the plurality of tissue anchors including a second barb angularly extending away from the first end portion of that tissue anchor, the first barb and the second barb each being configured to anchor the tissue anchor from the plurality of tissue anchors with respect to the bodily tissue.

20. The medical device of claim 15, wherein the filament is flexible.

* * * * *